United States Patent
Düppre

(10) Patent No.: US 9,440,758 B2
(45) Date of Patent: Sep. 13, 2016

(54) INSPECTION DEVICE FOR A PRODUCTION MACHINE

(75) Inventor: Theo Düppre, Kaiserslautern (DE)

(73) Assignee: Wipotec Wiege- und Positioniersysteme GmbH, Kaiserslautern (DE)

( * ) Notice: Subject to any disclaimer, the term of this patent is extended or adjusted under 35 U.S.C. 154(b) by 226 days.

(21) Appl. No.: 12/715,894

(22) Filed: Mar. 2, 2010

(65) Prior Publication Data

US 2010/0232570 A1   Sep. 16, 2010

(30) Foreign Application Priority Data

Mar. 10, 2009 (DE) .................. 10 2009 012 558

(51) Int. Cl.
*G01N 23/04* (2006.01)
*B65B 57/10* (2006.01)

(52) U.S. Cl.
CPC .................. B65B 57/10 (2013.01)

(58) Field of Classification Search
CPC . G01V 5/0016; G01V 5/0066; G01V 5/0008
USPC ........................................................ 378/57
See application file for complete search history.

(56) References Cited

U.S. PATENT DOCUMENTS

| | | | |
|---|---|---|---|
| 3,942,900 A | | 3/1976 | Garris |
| 3,958,078 A | * | 5/1976 | Fowler et al. ............ 348/127 |
| 5,568,715 A | | 10/1996 | Ebel et al. |
| 6,836,692 B2 | * | 12/2004 | Leavitt .................. B65B 5/04 53/498 |
| 2004/0028177 A1 | * | 2/2004 | Pipino ..................... 378/57 |
| 2007/0064041 A1 | * | 3/2007 | Sugahara ................. 347/19 |
| 2007/0164222 A1 | * | 7/2007 | Biel et al. ............... 250/358.1 |
| 2010/0018154 A1 | | 1/2010 | Laperche |

FOREIGN PATENT DOCUMENTS

| | | |
|---|---|---|
| DE | 102 49 962 A1 | 5/2004 |
| DE | 20 2007 000 471 U1 | 9/2007 |
| DE | 10 2009 008 708 A1 | 8/2010 |
| EP | 1 538 084 A1 | 6/2005 |
| JP | 2005/186967 A | 7/2005 |
| JP | 2007/199058 A | 8/2007 |
| JP | 2008/175691 A | 7/2008 |

OTHER PUBLICATIONS

JPO, Notification of Reasons for Refusal issued Dec. 6, 2012 in corresponding Japanese Patent Application No. 2010-051453 (3 pages).

\* cited by examiner

*Primary Examiner* — Hoon Song
(74) *Attorney, Agent, or Firm* — The Culbertson Group, P.C.

(57) ABSTRACT

The invention relates to an inspection device for a production machine, in particular, a bottling plant 1 with a filling device 7 or a filling and sealing device 13, with a stream of products (5) consisting of one or more columns, wherein the inspection device is arranged in the production machine, advantageously in the bottling plant 1, directly after the filling device 7 or the filling and sealing device 13 or before a separating device 23, so that the products 5 are inspected before the separation 23 or packaging 25 of the products 5. Furthermore, the invention relates to an inspection method for a production machine, in particular, for a bottling plant 1, in which an inspection device consisting of a source 17 and a sensor 19 scans several products 5 perpendicular or diagonal to the product motion B.

15 Claims, 3 Drawing Sheets

INSPECTION DEVICE FOR A PRODUCTION MACHINE

FIELD OF THE INVENTION

The invention relates to an inspection device for a production machine, in particular, a bottling plant, as well as to an inspection method for this device.

BACKGROUND OF THE INVENTION

Such inspection devices and methods are used, for example, in food processing. For example, in a production machine, in particular, a processing line or bottling and packaging line, food is filled in a single-layer matrix of cups or container chains generated by a deep-drawing process from a plastic surface. Here, the cups are tilled typically in a synchronized way by means of several filling nozzles arranged one next to and one behind the other, so that several cups can be processed simultaneously, in particular, a planar arrangement of a matrix consisting of several rows and several columns or a parallel product stream.

In the following, this parallel product stream is closed, for example, with a cover film and separated, for example, by means of a stamping device, into individual products. After the separating, partitioning, and conversion into a serial product stream, the products are usually packaged one above the other in multiple layers.

In order to exclude the presence of foreign bodies in the filled cups, the separated and packaged cups are typically examined by means of an x-ray inspection device. Disadvantageously, the examination with conventional inspection devices is time-intensive and slower than the actual processing speed of the bottling plant, so that the examination process slows down the overall processing speed. For example, in "PACK aktuell [Packaging news]", Jun. 1, 2008, x-ray inspection systems are presented that have a conveyor belt for products to be examined and can be added to a filling and packaging line after the separation and packaging of the products. If foreign bodies and/or incorrect fill levels are detected, already packaged boxes or other secondary packaging must be opened again and the defective products must be separated out from a series of several products that are usually arranged one above the other.

Furthermore, when examining products with conventional inspection systems, imprecise or incorrect results can occur due to the imprecise or undefined positioning of the individual products in secondary packaging.

SUMMARY OF THE INVENTION

Therefore, the present invention provides an inspection device for a production machine, in particular, for a bottling plant, as well as an inspection method for this device, with this method allowing an increase in the accuracy of the inspection at a high processing speed or throughput in an economical and simple way.

The invention provides both inspection devices and inspection methods.

According to the invention, the inspection device is integrated into the bottling plant as a fixed component, so that the advantageously synchronized product stream can be scanned by the inspection device before the products are separated. In this way, several products can be examined in one processing step, which allows a high processing speed due to this parallel processing of the product stream. Due to the products not yet being separated, the products are unambiguously defined in their positioning, so that imprecise or even incorrect examining or scanning results due to positional errors can be avoided.

In addition to access that is made more difficult or even prevented for operating personnel, the integration of the inspection device deep in the filling machine guarantees improved protection from a source, in particular, a radiation source, in the inspection device. In a further configuration of the invention, the inspection device is constructed as a scanning device, for example, as an x-ray, microwave, ultrasound, infrared device, etc. that advantageously has a scanning path essentially perpendicular to or at an angle to the product motion. In this way, in a simple and economical way, a high processing speed in sync with the processing speed of the filling device can be guaranteed. Through a non-parallel scanning path relative to the product motion, advantageously a shorter structural length and smaller width of the inspection device are possible, because the total width of the product stream no longer must be simultaneously covered with a correspondingly wide and long scanning field.

In addition, the smaller required extent of the scanning field requires a lower (transmission) power from the source, in particular, x-ray power, which advantageously also produces, in addition to the smaller structural form, even better radiation protection and also longer service life for the source, for example, an expensive x-ray tube.

In a preferred embodiment of the invention, the product stream is scanned in sync with the cycle of the filling device, that is, for example, during a stoppage or while the product stream is moving (stamping and filling elements are often moved along in sync), wherein the inspection device may also be performed before the beginning of a filling cycle, that is, for example, before a stoppage or advancing movement of the product stream. Obviously, however, it is also conceivable to scan the product stream continuously. Any pauses in the product movement or cycle may be bridged, for example, by the movement of the inspection device itself relative to the product motion or by pauses in the processing.

In a further configuration of the invention, the inspection device has a bidirectional operation, especially in the case of a scanning path that is not parallel to the product motion. In this way, pauses during the return motion of the inspection device can advantageously be avoided and the processing speed can be further increased.

In a further configuration of the invention, the inspection device has a source of radiation or waves (x-rays, microwaves, ultrasound, infrared, etc.) and a corresponding sensor which are each arranged fixed in place (complementary) relative to each other and/or underneath the product line. In the case of penetrating radiation, for example, x-ray radiation, the radiation source and sensor are mounted above and underneath the product stream positioned relative to each other such that the sensor lies in the region of the scanning field. The source and sensor here move advantageously in sync with each other across the entire scanning path, in order to guarantee an optimum scanning area across the product stream.

In the method according to the invention, the product stream is scanned with a scanning path that is not parallel to the product motion, for example, essentially perpendicular to the product motion, advantageously in a line, which allows, in a simple and economical way, quick and especially also parallel processing of an advantageously synchronized product stream. Simultaneously, through this scanning path lying perpendicular to or at an angle to the product motion, the accuracy of the scanning can be increased and the extent of the (static) scanning field can be bounded up to a short line covering only one or a few products—viewed in the direction of the product motion.

In this way, interfering stray effects can be reduced and in the case of a high-frequency source, for example, x-ray radiation, expensive shields (large lead aprons, etc.) for larger scanning fields can be avoided or reduced.

In a preferred construction of the method according to the invention, non-separated products advantageously in a matrix are scanned, so that their position is unambiguously defined. Additional advantageous configurations are described above for the inspection device according to the invention, without the processing steps explained here being limited to this device.

In a further configuration of the method according to the invention, the scanning, in particular, radioscopy, that is, for example, simultaneous movement of the camera and/or emitter, is preferably performed when the products or product stream is stopped (for example, during cycle pauses of the bottling plant), so that a lower radiation intensity is required and the image accuracy is increased. In addition, in this way, sloshing effects can be reduced.

Both the device according to the invention and also the method according to the invention can also be used in a radioscopy unit for, in addition to the known foreign body inspection and sealing seam inspection by means of determining the homogeneity and/or the surface level of the fill material in the container, the measurement and/or inspection of the fill quantity (for example, as an alternative to determining weight by means of a scale).

The invention will be explained in more detail below with reference to an embodiment shown in the drawing.

DETAILED DESCRIPTION OF PREFERRED EMBODIMENTS

Figure 1:
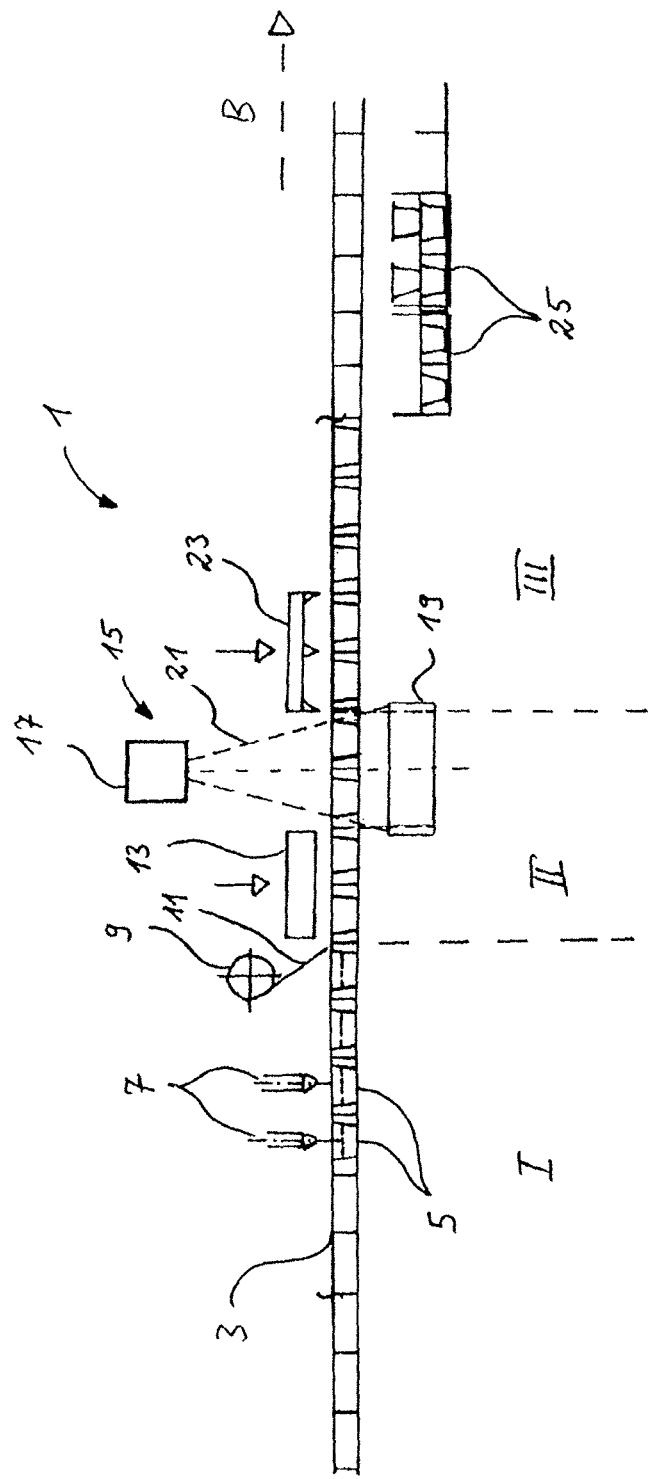
FIG. 1 is a side view of a production or filling and sealing line shown schematically with an inspection device according to the invention.

The production line or bottling plant 1 shown in FIG. 1 is used—especially with food—for filling, sealing, and packaging of cups 5 or similar containers.

Here, the cups 5 can be produced or have been produced, for example, by means of a deep-drawing process from a plastic surface 3, wherein fill material, especially food, is filled into these cups 5, which are open toward the top, by means of usually several filling nozzles 7, as shown, for example, in the embodiment, in a matrix of two rows and three columns.

According to this phase visible in section I, the cups 5 are closed at the top by means of a cover film 11 unwound from a roller 9 with the movement of and in the direction of movement B of the product stream by means of, for example, a thermal sealing unit and then examined indirectly or, as shown, directly by the inspection device 15 for contaminants and foreign bodies in the fill material, especially in food.

Figure 2:
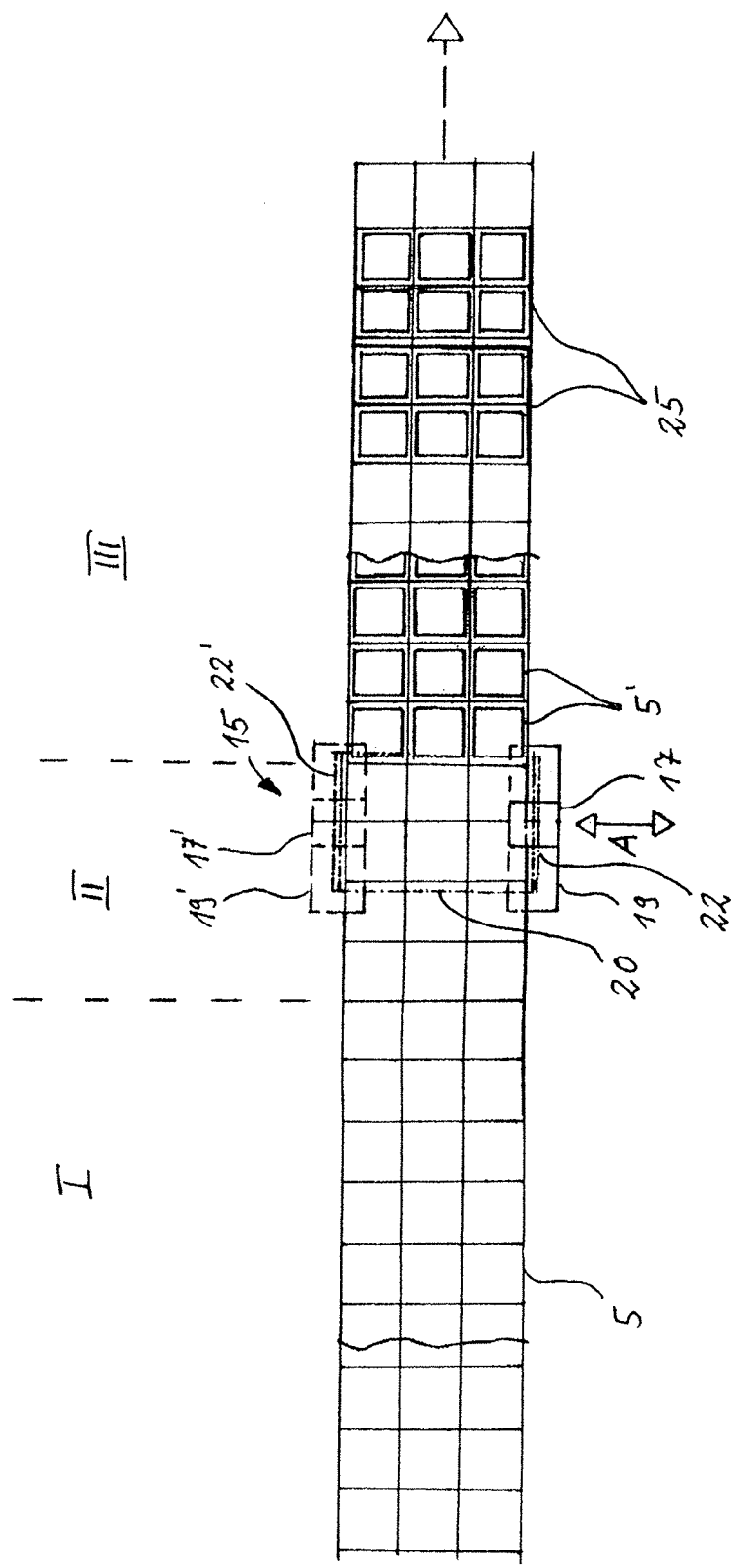
FIG. 2 is a top view of a production line according to FIG. 1.

As seen from FIGS. 1 and 2, the product stream in sections I and II consists of continuous flat container chains that are separated into individual cups 5' only after passing through the inspection device 15 in section III by means of a stamp 23 that can move downward from above. The separated cups 5' are then packaged in multiple layers in secondary packaging, such as, for example, boxes 25, wherein this can be realized with an arbitrary arrangement of the cups in the packaging, for example, as shown, in a flat 3×2 matrix and one above the other in a multiple-layer arrangement.

As seen in FIGS. 1 and 2, the product stream consists of continuous cups at least partially or even as a whole along its direction of movement B in the sections I and II, so that the position of the cups each located in a scanning area 20, for example, 3×2, is defined unambiguously both relative to each other and advantageously also in the entire product stream. Although in the example, a scanning area 20 across two rows and three columns is shown, it is obviously conceivable to form the scanning area across any number between one and more rows (or even in multiple layers) across all of the columns of the product stream.

In the depicted embodiment, the filling by means of filling nozzles 7 is synced, so that the product stream is moved in sync for filling nozzles 7 that are stationary in the direction of motion B or the filling nozzles are moved in sync accordingly for filling nozzles 7 that can move accordingly in direction B and for continuous product movement.

According to the invention, the inspection device 15 operates in sync with the synchronized motion named above, wherein both scanning or radioscopy is possible in the cycle of the filling and also in an offset cycle, that is, during pauses of the filling.

Advantageously, the scanning is performed at a time of relative standstill between the inspection device 15 and the product motion B viewed in the direction B, so that the necessary radiation intensity is reduced in this way, the image accuracy is increased, and sloshing effects are reduced or can even be prevented.

The inspection device 15 is composed of an x-ray radiation source 17 arranged, for example. above the product stream, with a scanning field spreading advantageously downward at an acute angle, and a camera or line sensor 19 arranged, for example, under the product stream in the area of this scanning field 21.

As seen in FIG. 2, for example, two rows of cups are covered in the direction B of the product stream, wherein, in the width of the product stream, there is only a small spread, in particular, a linear spread 22. In order to also scan the product stream in the width, the source 17 is moved in sync with the line sensor 19, as shown, perpendicular to direction A across the product stream from its lower, first position in FIG. 2 into an upper, second end position of the source 17', line sensor 19', and scanning line 22', so that in this way the total width of the product stream can be scanned in the field 20.

Figure 3:
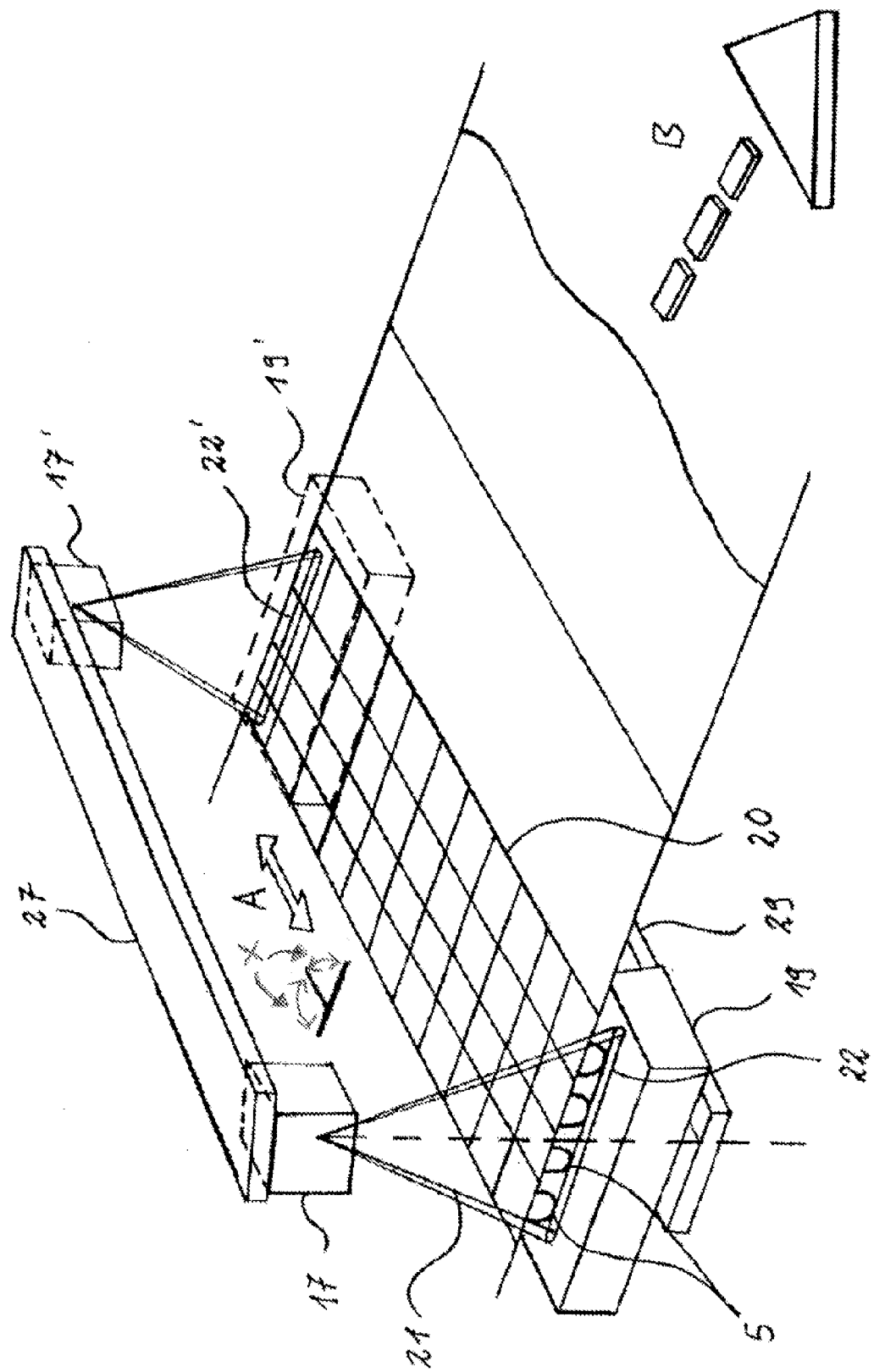
FIG. 3 is a three-dimensional view of an inspection device according to the invention as one detail of a production line according to FIGS. 1 and 2.

As seen from FIG. 3, the inspection device 15 has an upper linear bar 27 for the linear constant motion in the direction A for the source 17 and a lower linear bar 29 for the line sensor 19, wherein these bars allow, by means of suitable measures, a continuous motion of the source 17 and the sensor 19 in sync with each other across the entire scanning area 20.

The structural measures for realizing the inspection device 15 shown in the embodiment are obviously to be viewed as only schematic, wherein, for example, for a uniform, linear motion of the source 17 and then 19 relative to each other, various solutions not shown in more detail are evident for those skilled in the art. The corresponding linear rails or linear motors can be moved uniformly and in sync relative to each other controlled electronically, for example, without mechanical coupling of the source 17 and the sensor 19 with each other, wherein it is obviously also conceivable to use other solutions providing, for example, a mechanical coupling.

Advantageously, scanning can be performed not only in the forward movement in the direction of position 17', 19', 22' of the source, the sensor, the scanning line, but instead also in its return motion up to its position shown with the reference symbols 17, 19, 22. Through this bidirectional scanning during the forward and backward movement along the axis A perpendicular to the product movement B, a higher possible processing speed can be achieved.

In addition, despite cycle-synced movement relative to the filling device or filling nozzles 7, the respective movement of the source 17 and the sensors 19 and thus of the scanning line 22 is to be already set before a relative standstill between the inspection device 15 and product stream with respect to its direction of motion B, in order to obtain a relative standstill between the inspection device 15 and the product stream in the direction B only when reaching the scanning line 22 of the first cup column arranged at the edge (in the shown example, the outer columns of the three-column product stream).

If a contaminant, a foreign body, or another undesired result, such as. for example, incorrect fill level, etc., of one or more cups is detected during the scanning by means of the inspection device 15, these cups can be separated out in the shown system according to the invention advantageously already before packaging, that is, after the separation of the cups into individual products or even after the partitioning into a serial product stream, without the unpacking from secondary packaging and removal of the defective individual products otherwise necessary for radioscopy on the secondary packaging being required for this process.

By means of the method according to the invention and the device according to the invention, it is possible based on the parallel or even flat processing of the product stream to determine the fill level of the fill material exactly by means of the inspection device 15, because the geometric arrangement of the cups relative to each other is precise during the scanning and incorrect results due to rotated or displaced positioning like in examinations of individual cups in a serial, partitioned product stream or in the secondary packaging can be avoided.

Also, if a scanning path A is shown perpendicular to the product movement B in the embodiment, it is obviously also conceivable to select the scanning path at a different angle enclosing an angle>0 to the motion B (depicted in FIG. 3 as angle X) and to nevertheless allow the advantages mentioned above.

It should be noted, in particular, that the plant according to the invention is also possible with an inspection device operating in the direction of the product motion B, wherein, for example, in this case, the inspection device has no scanning path A, but instead a perpendicular or angled scanning line or scanning field reaching across the entire product stream width. In this configuration, the advantages explained above as essential, such as, for example, quicker processing, better shielding through structural integration, preferred higher inaccessibility for the operating personnel, etc., can be achieved through the arrangement of such an inspection device in the inspection stream indirectly or directly after the filling unit and possibly the sealing unit or before the partitioning.

As used herein, the terms "comprising," "including," "having," and the like are to be understood to be open-ended, that is, to mean including but not limited to.

The above described preferred embodiments are intended to illustrate the principles of the invention, but not to limit the scope of the invention. Various other embodiments and modifications to these preferred embodiments may be made by those skilled in the art without departing from the scope of the present invention.

The invention claimed is:

1. A production line comprising:
   (a) a plurality of filling devices adapted to fill a product stream comprising a number of containers connected in a grid;
   (b) a locomotion device for moving the product stream from the plurality of filling devices in a downstream direction;
   (c) an inspection device located in the downstream direction from the filling devices, wherein
      (i) the inspection device is adapted to inspect the containers in the product stream after the containers are filled by the filling devices, but before the containers undergo a first separation from the connected grid of the product stream into individual containers;
      (ii) the inspection device is further adapted to inspect a number of discrete arrays of containers within the product stream, each array of containers comprising at least two rows oriented perpendicularly to the downstream direction and at least one column oriented along the downstream direction;
      (iii) the inspection device comprises a scanning device with a scanning path, along which the scanning device moves so as to scan the containers in the array, wherein the inspection device is adapted to move such that the scanning path is at an angle greater than 0° to the downstream direction;
      (iv) the inspection device further comprises a source of radiation or waves and a sensor, the source and sensor arranged in a fixed location with respect to each other above and underneath the product stream, and adapted to move across the scanning path in sync with each other; and
   (d) a separation device for conducting a second separation separating one or more undesired individual containers from the product stream after the products have been inspected by the inspection device.

2. The production line of claim 1, wherein the scanning device moves bi-directionally along the scanning path including scanning during a first movement along the scanning path and scanning during a second movement returning along the scanning path.

3. The production line of claim 1, wherein the inspection device is constructed as a radioscopy unit.

4. The production line of claim 1, wherein the plurality of filling devices fills the containers with a foodstuff.

5. The production line of claim 1, wherein the source of radiation is adapted to emit X-rays, and the sensor is adapted to detect X-rays.

6. The production line of claim 1 in which each array of containers comprises at least two rows and two columns.

7. The production line of claim 1 in which the inspection device has a scanning field that spans the at least two rows of the arrays of containers.

8. An inspection method for inspecting a connected grid of products in a moveable production line, the method comprising:

(a) moving an array of connected products into a scanning area, the array of products comprising at least two rows oriented perpendicularly to the downstream direction and at least one column oriented along the downstream direction;

(b) scanning the array of products in the scanning area, the step of scanning the products further comprising:

(i) moving an inspection device along a scanning path that is at an angle greater than 0° to a downstream direction of the production line, the inspection device comprising a radiation source and a radiation sensor;

(ii) while moving the inspection device, radiation source, and radiation sensor in step (b)(i), emitting radiation from the radiation source, so as to contact each product in the array of products and the radiation sensor; and (iii) identifying, from information gathered by the radiation sensor, whether an abnormality exists in the array of products;

(c) after scanning the array of products, separating the array of products into individual products; and (d) after separating the array of products, separating one or more undesired products from product stream.

9. The method of claim 8, wherein the scanning device moves bi-directionally along a scanning path including scanning during a first movement along the scanning path and scanning during a second movement returning along the scanning path.

10. The method of claim 8, further comprising removing the array from the scanning area after performing the scanning step in part (b), and moving a second array of products into the scanning area.

11. The method of claim 8, wherein the moveable production line is a foodstuff packaging line, and the products comprise containers filled with a food product.

12. The method of claim 8, wherein the abnormal condition comprises the presence of a contaminant or foreign body within one or more of the products in the array of products.

13. The method of claim 8, wherein the abnormal condition comprises an incorrect fill level of one or more of the products in the array of products.

14. The method of claim 8 in which the array of products comprises at least two rows and two columns.

15. The method of claim 8 in which the inspection device has a scanning field that spans the at least two rows of the array of products.

* * * * *